United States Patent
Dagsland

(10) Patent No.: US 8,025,051 B2
(45) Date of Patent: Sep. 27, 2011

(54) DELIVERY DEVICE

(75) Inventor: Allan Dagsland, Lund (SE)

(73) Assignee: Astrazeneca AB, Sodertalje (SE)

( * ) Notice: Subject to any disclaimer, the term of this patent is extended or adjusted under 35 U.S.C. 154(b) by 489 days.

(21) Appl. No.: 12/097,969

(22) PCT Filed: Dec. 21, 2006

(86) PCT No.: PCT/SE2006/001466
§ 371 (c)(1),
(2), (4) Date: Jun. 18, 2008

(87) PCT Pub. No.: WO2007/073302
PCT Pub. Date: Jun. 28, 2007

(65) Prior Publication Data
US 2008/0289653 A1 Nov. 27, 2008

(30) Foreign Application Priority Data

Dec. 23, 2005 (SE) ...................................... 0502909

(51) Int. Cl.
*A61M 16/00* (2006.01)
*A61M 15/00* (2006.01)
*B67D 1/08* (2006.01)
(52) U.S. Cl. ................. 128/203.15; 128/203.12; 222/149
(58) Field of Classification Search ............. 128/203.25, 128/203.29, 203.12, 203.23, 203.21; 604/58; 239/338, 500, 502; 222/148–151
See application file for complete search history.

(56) References Cited

U.S. PATENT DOCUMENTS

| | | | | |
|---|---|---|---|---|
| 5,033,463 A | * | 7/1991 | Cocozza | 128/203.21 |
| 6,116,469 A | * | 9/2000 | Wallays et al. | 222/148 |
| 6,655,380 B1 | * | 12/2003 | Andersson et al. | 128/203.15 |
| 6,810,875 B2 | * | 11/2004 | Staniforth et al. | 128/203.15 |
| 2007/0246044 A1 | * | 10/2007 | Peng et al. | 128/203.15 |

FOREIGN PATENT DOCUMENTS

| | | |
|---|---|---|
| EP | 0573128 | 12/1993 |
| EP | 1163920 | 12/2001 |
| EP | 1454647 | 9/2004 |
| EP | 1454647 A2 * | 9/2004 |
| WO | WO 01/95963 | 12/2001 |

OTHER PUBLICATIONS

International Patent Application No. PCT/SE2006/001466: International Search Report and Written Opinion; Date of Mailing: Mar. 13, 2007.

* cited by examiner

*Primary Examiner* — Justine Yu
*Assistant Examiner* — Rachel Young
(74) *Attorney, Agent, or Firm* — Finnegan, Henderson, Farabow, Garrett & Dunner, LLP

(57) ABSTRACT

A delivery device for administering particulate medicaments, such as dry powder. The delivery device comprises a body and a flow path comprising a chamber with an inlet and an outlet for the stream of air. The chamber is rotatable in relation to the body. Dislodging means are arranged in contact with the inner surface of the chamber. The dislodging means and the chamber are relatively rotatable in relation to one another, such that the inside of the chamber is cleaned by the dislodging means when the dislodging means and the chamber are rotated in relation to one another.

10 Claims, 1 Drawing Sheet

DELIVERY DEVICE

CROSS-REFERENCE TO RELATED APPLICATIONS

This application is a national phase application under 35 U.S.C. §371 of PCT International Application No. PCT/SE2006/001466, filed Dec. 21, 2006, which claims priority to Swedish Application Serial No. 0502909-5, filed Dec. 23, 2005. The contents of each of these applications are incorporated herein by reference in their entirety.

TECHNICAL FIELD

The present invention relates to a delivery device, such as a dry powder inhaler, for administering particulate medicaments, and to cleaning such a delivery device.

BACKGROUND

In some dry powder inhalers the mouthpiece is partly cleaned from retained drug powder by a wiper that wipes the flat horizontal surface of the mouthpiece insert upon rotation of the mouthpiece. The wiper reduces powder retention in the mouthpiece significantly, verifying that the principle of rinsing with a wiper works. Powder, which may have accumulated on the inner surfaces of the inhaler, is dislodged from those surfaces prior to the next inhalation. In addition, by configuring the inhaler such that the mouthpiece is rotated automatically when the mouthpiece insert holder is removed, it is not necessary to rely upon the user to remember to rotate the mouthpiece prior to each inhalation.

This product improvement has resulted in a correspondingly lower build-up of retained drug powder inside the inhaler, which has significantly lowered the risk of retention losses during use. However, it is clear that further reduction of retained drug powder inside other parts, such as the mouthpiece, of the inhaler is desirable. Improvement of the cleaning function would give a further increased product robustness and reliability.

Mouthpieces for dry powder inhalers use among other means helical devices for breaking up the particulate medicament that is being inhaled by the patient. Cleaning of the channel of the mouthpiece is especially difficult when such helical device is used.

WO 01/95963 discloses a mouthpiece for a particulate inhaler. The known device discloses a mouthpiece provided with a helical member disposed between the inlet and the outlet of the mouthpiece. By air drawn by a user, the helical member undergoes an axial movement between a first and a second position such that it restricts the build up of medicament on the inside of the mouthpiece.

Cleaning in this known device is achieved by axial movement of the helical member in relation to the mouthpiece. The movement of the helical member in the axial direction requires that the length of the mouthpiece is long enough to enable such movement.

In this known device, the axial movement of the helical member is achieved by the force of the air drawn by the user. Cleaning performance thus depends on the flow rate achieved by the patient. The helical member is retained in its initial position by the force of a resilient arm. Thus, the efficiency of the cleaning procedure depends on the user's ability to breath strong enough to overcome the force of the spring and thereby achieve the axial is movement of the helical member. If the device is used by a patient with poor breathing capacity, the cleaning effect might be poor. In that case, medicaments might be built up in the mouthpiece, thus demanding a higher flow rate after each inhalation to achieve a clean mouthpiece. A further risk is that if medicaments continue to be built up on the inside of the inhaler after each inhalation, the helical member might get stuck during the axial movement. Further, for every inhalation a part of the force used by the patient is consumed by the cleaning device, thus leaving less to actually inhale and deagglomerate the dose.

SUMMARY

A delivery device for administering particulate medicaments includes a body and a flow path defined by a plurality of surfaces through which a stream of air is drawn by a user. The flow path comprises a chamber with an inlet and an outlet for the stream of air. The chamber is rotatable in relation to the body. The delivery device comprises dislodging means in contact with the inner surface of the chamber. The dislodging means and the chamber are relatively rotatable in relation to one another such that, the inside of the chamber is cleaned by the dislodging means when the dislodging means and the chamber are rotated in relation to one another. Building up of medicament on the inside of the chamber is thus restricted.

In another embodiment, the chamber is at least partly defined by a mouthpiece insert. The dislodging means and the mouthpiece insert are relatively rotatable in relation to one another such that the inside of the mouthpiece insert is cleaned by the dislodging means when the dislodging means and the mouthpiece insert are rotated in relation to one another. Building up of medicament on the inside of the mouthpiece insert is thereby restricted.

In another embodiment, the delivery device further includes a helical member arranged between the inlet and the outlet of the delivery device, for imparting a rotational movement to the airflow drawn through the delivery device. The helical member is arranged in contact with the inside of the mouthpiece insert. The helical member is part of the dislodging means. The inner surface of the mouthpiece insert is cleaned by the helical member when the dislodging means and the mouthpiece insert are rotated in relation to one another.

In another embodiment, the helical member has a plurality of intertwined helical sections.

In yet another embodiment, the helical member has two intertwined helical sections.

In another embodiment, the helical member comprises biasing means for applying a force on the inside of the mouthpiece insert substantially perpendicular in relation to the longitudinal axes of the delivery device.

In yet another embodiment, the intertwined helical sections are resilient, thereby applying a force on the inside of the mouthpiece insert substantially perpendicular in relation to the longitudinal axes of the delivery device.

In another embodiment, the mouthpiece insert comprises a first portion and a second portion, and the dislodging means further comprises a dislodging member, arranged in contact with the inner surface of the first part of the chamber, and the helical member is arranged in contact with the inner surface of the second part of the mouthpiece, such that the inner surfaces of the mouthpiece insert portions are cleaned by the member and by the helical member, respectively, when the dislodging means and the mouthpiece insert are rotated in relation to one another.

In another embodiment, the delivery device further comprises a mouthpiece insert holder, the mouthpiece insert and the mouthpiece insert holder each comprise parts that engage one another, such that the dislodging means and the mouthpiece insert are relatively rotated in relation to one another when screwing or unscrewing the mouthpiece insert holder. The cleaning occurs automatically when the inhaler is opened. Since the mouthpiece insert and the body is relatively rotated in relation to one another automatically when the mouthpiece insert holder is screwed off, it is not necessary to rely upon the user to remember to rotate the mouthpiece prior to each inhalation.

In another embodiment, the dislodging means and the body each includes parts that engage one another, such that the body and the mouthpiece insert are firmly attached to one another.

In another embodiment, the dislodging means comprises a protruding member arranged to engage with a cut-out in the body, such that the body and the insert are firmly attached to one another.

Another aspect of the invention relates to a method for cleaning a delivery device. The delivery device comprises a flow path defined by a plurality of surfaces through which a stream of air is drawn by a user, and a body. The flow path comprises a chamber with an inlet and an outlet for the stream of air. The chamber is rotatable in relation to the body. Further, the delivery device comprises dislodging means arranged in contact with the inner surface of the chamber. The method comprises rotating the dislodging means and the chamber in relation to one another, such that the inside of the chamber is cleaned by the dislodging means, whereby building up of medicament on the inside of the chamber is restricted.

In another embodiment, the method comprises the step of rotating the dislodging means and the mouthpiece insert in relation to one another prior to inhalation. Since the cleaning procedure is achieved before and not during inhalation, the procedure is independent of the airflow drawn by the user.

In yet another embodiment, the method comprises the step of applying a force on the inside of the mouthpiece by biasing means, the force being substantially perpendicular in relation to the longitudinal axis of the delivery device.

The method and the delivery device of the present invention may be used with any suitable form of powder, including powders introduced into the air stream in the raw state or as conglomerate, micronized or ordered mixture particles. Furthermore, the active ingredient or ingredients of the powder may be diluted with one or more substances such as lactose and may include substances for the treatment of various conditions, not necessarily respiratory conditions. Indeed, the powder can include genetic material and need not be restricted to human use only.

Medicaments suitable for administration by the powder inhaler of the present invention are any which may be delivered by inhalation and include for example β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, indacaterol, procaterol, broxaterol, picumeterol, carmoterol (TA-2005), mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; is cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

DETAILED DESCRIPTION

Figure 1:
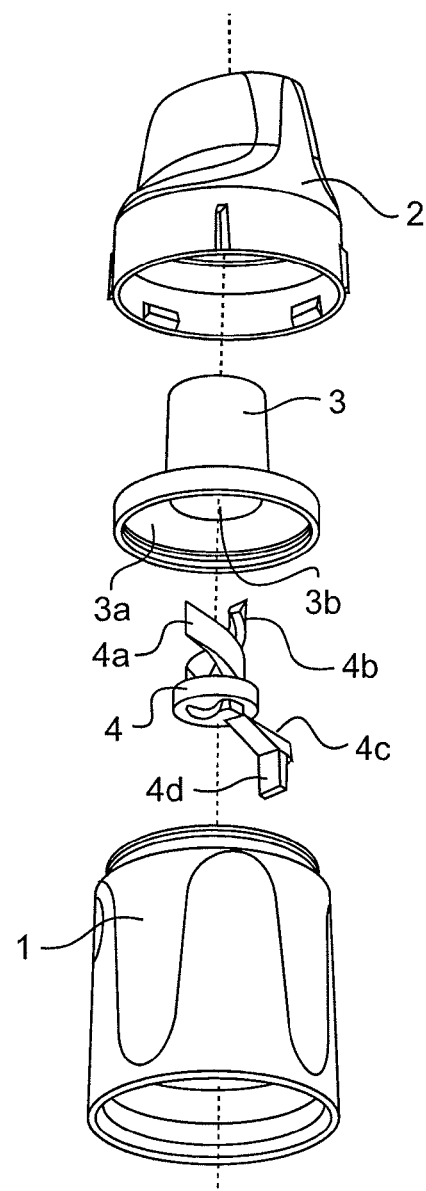
FIG. 1 shows parts of a delivery device.

FIG. 1 shows details of a delivery device. The delivery device comprises a body 1 with a smooth top, and a chamber at least partly defined by a mouthpiece insert 3, and dislodging means 4 comprising a helical member and a dislodging member 4c. The dislodging member 4c may be of any suitable shape, such as a wiper arm. The mouthpiece insert 3 and the dislodging means 4 are mounted relatively rotatable in relation to one another. The dislodging means 4 is firmly attached to the body, and the mouthpiece insert 3 is attached to the mouthpiece insert holder 2. When the mouthpiece insert holder 2 is unscrewed and thus undergoes a rotational movement, the mouthpiece insert 3 also undergoes a rotational movement and the mouthpiece insert 3 and the dislodging means are rotated relative to one another. The helical member 6 is arranged in close contact with the inside of a portion 3b of the mouthpiece insert 3, and the dislodging member 4c is arranged in close contact with the inside of another portion 3b of the mouthpiece insert. Thus, during the relative rotational movement achieved by unscrewing the mouthpiece insert holder 2, the helical member 6 wipes off any powder left on the inside of the portion 3b of the mouthpiece insert. At the same time, the dislodging member 4c wipes off any powder left on the inside of the portion 3a of the mouthpiece. The helical member has two intertwined helical sections (4a, 4b).

Figure 2:
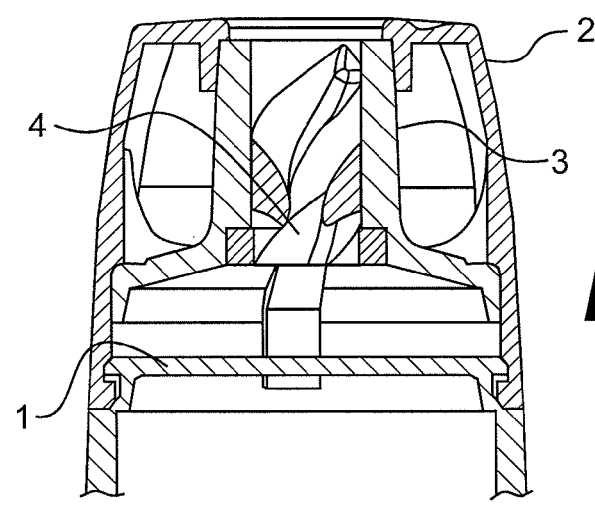
FIG. 2 shows a cross-section of the top of a delivery device.

FIG. 2 shows a cross-section of the top of the device. The device comprises an insert holder 2 and an insert 3 with a channel, and dislodging means 4 comprising a helical member and a dislodging member 4c, in this embodiment shown as a wiper arm. The helical member and the dislodging member 4c are used for cleaning the portion 3b of the mouthpiece insert 3, and the portion 3a of the mouthpiece insert 3, respectively. The dislodging means 4 is in this embodiment firmly attached to the body 1 by a protruding member 4d, arranged to engage with a cut-out (not shown) in the body 1. The mouthpiece insert 3 is attached to mouthpiece insert holder 2 and therefore rotates automatically in relation to the dislodging means 4 when the mouthpiece insert holder 2 is unscrewed and thus undergoes a rotational movement. The body 1 has a smooth top to minimize dead space.

The invention claimed is:
1. A delivery device for administering particulate medicament to a subject, the device comprising:
 a body defining at least a portion of a flow path for a stream of air drawn through the device, the flow path including a chamber defined at least partially by a surface that is rotatable with respect to the body, the chamber having an inlet and an outlet; and a medicament dislodger that is attached to the body and disposed within the chamber, wherein the dislodger is in contact with a wall at least partially defining the chamber and a mouthpiece insert, the dislodger configured to remove particulate medicament from the wall as the surface is rotated with respect to the body and the mouthpiece insert, wherein the dislodger includes a helix positioned between the inlet and the outlet of the chamber and in contact with the wall of the mouthpiece insert, the helix being arranged to remove particulate medicament from the wall of the mouthpiece insert during rotation of the dislodger with respect to the mouthpiece insert and impart a rotational movement to the air drawn through the delivery device.

2. The delivery device of claim 1, wherein the dislodger includes a protrusion arranged to engage a notch in the body, such that the body and the dislodger are firmly attached to one another.

3. The delivery device of claim 1, wherein the surface that is rotatable with respect to the body includes the wall of the mouthpiece insert.

4. The delivery device of claim 1, further comprising a mouthpiece insert holder arranged to reversibly rotationally engage the mouthpiece insert, wherein the mouthpiece insert holder is configured to rotationally engage the mouthpiece insert and to rotate the mouthpiece insert relative to the dislodger during rotational engagement and rotational disengagement of the mouthpiece insert holder and the mouthpiece insert.

5. The delivery device of claim 1, wherein the helix is biased to apply a force to the wall of the mouthpiece insert, and the force is substantially perpendicular to a longitudinal axis of the mouthpiece insert.

6. The delivery device of claim 1, wherein the mouthpiece insert includes a first portion and a second portion and the dislodger further includes an extension coupled to the helix, wherein the extension is arranged to contact an inner surface of the first portion of the mouthpiece insert and the helix is arranged to contact an inner surface of the second portion of the mouthpiece insert, and wherein the extension is arranged to remove particulate medicament from the inner surface of the first portion of the mouthpiece insert and the helix is arranged to remove particulate medicament from the inner surface of the second portion of the mouthpiece insert during rotation of the dislodger with respect to the mouthpiece insert.

7. The delivery device of claim 1, wherein the helix includes a multiplicity of intertwined helical sections.

8. The delivery device of claim 7, wherein the helix includes two intertwined helical sections.

9. The delivery device of claim 7, wherein the intertwined helical sections are resilient.

10. The delivery device of claim 7, wherein the intertwined helical sections are arranged to apply a force to the inner surface of the first portion of the mouthpiece insert, and the force is substantially perpendicular to a longitudinal axis of the mouthpiece insert.

\* \* \* \* \*